United States Patent [19]

Johnson et al.

[11] Patent Number: 5,402,460
[45] Date of Patent: Mar. 28, 1995

[54] THREE-DIMENSIONAL MICROTOMOGRAPHIC ANALYSIS SYSTEM

[75] Inventors: Roger H. Johnson, North Bend; Alan C. Nelson, Redmond; Robert M. Fisher, Seattle, all of Wash.

[73] Assignee: University of Washington, Seattle, Wash.

[21] Appl. No.: 100,778

[22] Filed: Aug. 2, 1993

[51] Int. Cl.⁶ .................. G01N 23/087; G01N 23/083; A61B 6/03
[52] U.S. Cl. ......................................... 378/10; 378/5; 378/901
[58] Field of Search .................. 378/4, 5, 10, 137, 901

[56] References Cited

U.S. PATENT DOCUMENTS

| | | | |
|---|---|---|---|
| 4,833,698 | 5/1989 | Flannery et al. | 378/19 |
| 5,023,895 | 6/1991 | McCroskey et al. | 378/4 |
| 5,044,001 | 8/1991 | Wang | 378/43 |
| 5,068,882 | 11/1991 | Eberhard | 378/4 |
| 5,245,648 | 9/1993 | Kinney et al. | 378/43 |
| 5,259,013 | 11/1993 | Kuriyama et al. | 378/43 |

OTHER PUBLICATIONS

R. H. Johnson et al., "Instrument Design and Image Reconstruction For A Laboratory X-Ray Microtomograph", *Abstracts for the Proceedings of the XIIth International Congress for Electron Microscopy*, Aug. 12, 1990.
V. E. Cosslett et al., "The X-ray Shadow Microscopy", *Journal of Applied Physics* 24(5):616–623, 1953.
S. M. Gruner et al., "CCD and Vidicon X-ray Detectors: Theory and Practice", *Review of Scientific Instruments* 60(7):1545–1551, 1989.
L. A. Feldkamp et al., "Practical Cone-beam Algorithm", *Journal of the Optical Society of America* 1(6):612–619, 1984.
L. A. Feldkamp et al., "Fundamental Aspects of Micro-CT in Cone-beam Geometry", *Review of Progress in Quantitative Nondestructive Evaluation 8A*, Plenum, N.Y., pp. 381–388, 1989.
P. Rizo et al., "Cone-beam 3-D Reconstruction with Double Circular Trajectory", *Materials Research Society Symposium Proceedings*, 217, 117–122, 1991.
Cheng, P. C. et al. "Projection Microscopy and Microtomography using X-rays", *Scanning 13 (Supplement I)*:I-10–I-11, 1991.
T. H. Lin et al., "A Helical Cone-beam Reconstruction Algorithm for X-ray Microtomography", *Scanning 13 (Supplement I)*:I-11–I-13, 1991.
R. E. Alvarez et al. "Energy-selective Reconstructions in X-ray Computerized Tomography", *Physics in medicine and Biology* 21(5):733–744, 1976.
B. Jacobson, "Dichromatic Absorption Radiography. Dichromography", *Acta Radiologica* 39:437–452, 1953.
J. L. Kuhn et al., "Evaluation of a Microcomputed Tomography System to Study Trabecular Bone", *Journal of Orthopedic Research* 8:833–842, 1990.

(List continued on next page.)

*Primary Examiner*—Paul M. Dzierzynski
*Assistant Examiner*—David Vernon Bruce
*Attorney, Agent, or Firm*—Christensen, O'Connor, Johnson & Kindness

[57] ABSTRACT

A microtomographic system (10) for generating high-resolution, three dimensional images of a specimen (16) is disclosed. The microtomograph system includes an x-ray generator (12) that produces an x-ray beam (14), a specimen holder (18) that holds the specimen in the beam, and an x-ray detector (20) that measures the attenuation of the beam through the specimen. Two projections of each view of the specimen are made with this microtomographic system. Each projection is made with a different intensity x-ray beam. After the projections of one view of the specimen are made, the specimen is rotated on the specimen holder and another set of projections are made. The projections of each view of the specimen are analyzed together to provide a quantitative indication of the phase fraction of the material comprising the specimen. The projections of the different views are combined to provide a three-dimensional image of the specimen.

12 Claims, 4 Drawing Sheets

OTHER PUBLICATIONS

F. H. Seguin et al., "X-ray Computed Tomography with 50-micron Resolution", *Applied Optics* 24(23):4117–4123, 1985.

J. M. Boone et al., "A Fluoroscopy-based Computed Tomography Scanner for Small Specimen Research", *Investigative Radiology* 28(6):539–544, 1993.

J. H. Kinsey et al., "High-Repetition Rate Volumetric X-ray CT Scanning", *IEEE Transactions on Nuclear Science*, NS-28(2):1732–1735, 1981.

A. Y. Sasov, "An Integrated PC-based Image Analysis System for Microtomography and Quantitative Analysis of Inner Micro-object Structure", *Journal of Microscopy*, 156(1):91–103, 1989.

G. Fuhrmann et al., "X-ray Microtomography with SEM for Laboratory Material Research", *Proceedings of the 1991 Industrial Computer Tomography Topical Conference, American Society for Nondestructive Testing, Columbia, Ohio., 1991*.

S. Takuso et al., "X-ray Tomography for Microstructural Objects", *Applied Optics* 20(22):3880–3883, 1981.

J. C. Buckland-Wright, "Quantitative Microfocal Radiography in Medicine, Biological Research, and the Quality Control Industry:", *SPIE*, vol. 368, pp. 9–16, 1982.

THREE-DIMENSIONAL MICROTOMOGRAPHIC ANALYSIS SYSTEM

FIELD OF THE INVENTION

This invention relates generally to a microtomograph and, more particularly, to a microtomographic system capable of producing three-dimensional images of microscopic specimens with a high degree of resolution and of provideing a quantitative measurement of the composition of the material comprising the specimen being imaged.

BACKGROUND OF THE INVENTION

A microtomograph is a device that produces a high spatial resolution image of a specimen such as biological tissue, an electronic component, or a geological sample. One type of microtomograph in use today is the x-ray microtomograph. This device typically includes an electron gun that produces a high voltage electron beam, which is directed to strike a solid or thin foil target formed from a metal having a relatively high atomic-number. The impact of these high energy electrons on atoms within the target foil causes an x-ray beam to be emitted by the target. The microtomograph is configured so that the x-ray beam is directed toward the specimen being imaged. An x-ray sensitive detector is located beyond the specimen to monitor the transmission of x-rays through the specimen. The signal produced by the detector in response to the x-rays is then processed to generate an image of the specimen. Currently, most microtomographs are capable of producing specimen images at a spatial resolution on the order of 50-200 microns.

In the past few years, it has been recognized x-ray microtomographs can be constructed from scanning electron microscopes (SEMs). An SEM has an electron gun that can be configured to produce an electron beam that is directed toward a foil target, causing an x-ray beam to be emitted for use in imaging a specimen. However, a disadvantage of some of these microtomographic systems constructed from SEMs is that owing to the nature of the construction, the specimen and detector can only be positioned in a few locations relative to the x-ray source. This restriction limits the flexibility in the size of specimens that may be accommodated and the spatial resolution of the resultant images.

While current x-ray imaging devices, including x-ray microtomographs constructed out of converted SEMs, have proved useful devices for generating relatively high-resolution images, they are not without limitations. One limitation of most x-ray microtomographs is that they can only produce two-dimensional images. The only way that three-dimensional images can be created with such systems is by making a series of two-dimensional slice images and then interpolating the specimen structure between the slice lines.

Attempts have been made to design microtomographs capable of directly producing three-dimensional images. Some of these devices are designed to simultaneously expose the specimen being viewed to two or more x-ray beams. A disadvantage of these devices is that they require multiple x-ray beam generators and a complementary number of x-ray detectors. The expense as well as the practicality of assembling the large number of components these microtomographs require has limited their potential for providing three-dimensional high resolution images.

Another disadvantage of currently available microtomographs is that they are unable to generate images providing quantitative information about the composition, or phase fractions, of the material comprising the specimen being viewed. While many microtomographs are capable of generating images that qualitatively depict the existence of two or more phases of a specimen, it has been difficult to use a microtomograph to generate a quantitative value indicating, for example, the ratio of hard tissue to soft tissue in a biological tissue specimen. This ability to quantify the phase fractions of the tissue is important for the study of, for example, bone structure and diseases such as osteoporosis. Although attempts have been made to construct microtomographs that provide quantitative data about the specimen being imaged, the current processes only provide data that serve as an estimate of the phase fraction of the material, but do not provide data that precisely quantify the phase fraction of the material being imaged.

The inability of current microtomographs to provide such precise phase fraction related quantitative information about the specimen being imaged, as well as the lack of simple, cost effective microtomographs capable of directly making three-dimensional images, has thus limited the use of these instruments.

SUMMARY OF THE INVENTION

This invention relates to a new and useful microtomographic system. More particularly, this invention relates to a microtomographic system capable of producing three-dimensional images, depicting the features of the specimen being imaged with a spatial resolution in the; micron range, and providing quantitative information about the composition, i.e., the phase fractions, of the material comprising a specimen.

A microtomographic system in accordance with this invention includes an x-ray generator, a specimen holder, an x-ray detector, and a processor that is connected to the x-ray detector for monitoring the detected x-rays. The x-ray generator, which may be in the form of a reconfigured SEM electron beam focusing column, is constructed to emit x-ray beams that have different energy spectra. In one particular embodiment of the invention, the electron beam focusing column is configured to direct the electron beam outward, so that the resultant x-ray beam is directed at an angle that is offset from the vertical. The x-ray generator is further configured to shift the beam it creates so that the specimen may be imaged with beams that originate from different source locations. The specimen holder is designed to support the specimen so that its can be both rotated in an axis perpendicular to the center of the x-ray beam, and laterally displaced. The x-ray detector preferably comprises a charge coupled device. The processor produces three-dimensional images of the specimen based on the data received from the x-ray detector and analyzes the data to generate a quantitative indication of the composition of the matter forming the specimen.

High resolution images are obtained with the microtomographic system of this invention by producing multiple cone beam projections from a single view of the specimen, i.e., when it is in a fixed angular orientation. Each projection of the specimen when it is in a given position is made using an x-ray beam of different energy spectral characteristics. After a set of projections of a first view of the specimen are produced, the specimen is incrementally rotated and a second set of projections of a second view of the specimen are made. This process is repeated until multiple sets of projections of different views of the specimen at different angular rotations through 360° have been obtained.

The individual projections of each view of the specimen are processed by comparing the x-ray absorption characteristics of the specimen at the different peak x-ray energies to those of a series of phantom specimens containing known and systematically varying path lengths of the phases of interest. This comparison yields a quantitative measurement of the composition, or distinct phase fractions, for the different types of material that comprise the specimen, as depicted in that particular view of the specimen. These phase fraction data are used to produce an intermediate, processed projection of the specimen from that particular view. The processed projections of the different views of the specimen are then collectively processed to produce three-dimensional images of the specimen. These images, in addition to depicting surface contours of the specimen, also provide information regarding the concentrations or phase fractions of its internal constituent materials. Depending on the relative placement of the x-ray source and detector, these images may depict the features of the specimen with micron-order resolution.

An advantage of the microtomographic system of this invention is that it provides means for producing high-resolution, three-dimensional images of a specimen from which quantitative information about the phase fractions of the material forming the specimen can be obtained. Still another feature of the invention is that the x-ray beams are generated for interaction with the specimen in an ambient environment. Thus, this microtomograph is well suited for making images of biological tissue and other specimens that contain moisture, which cannot be imaged in a vacuum, since depressurization would cause their character to change. Furthermore, the feature of constructing the x-ray generator so that the electron beam is deflected in a non-vertical direction prior to striking the associated foil target enhances the performance of the embodiments of this invention that are built from SEMs.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
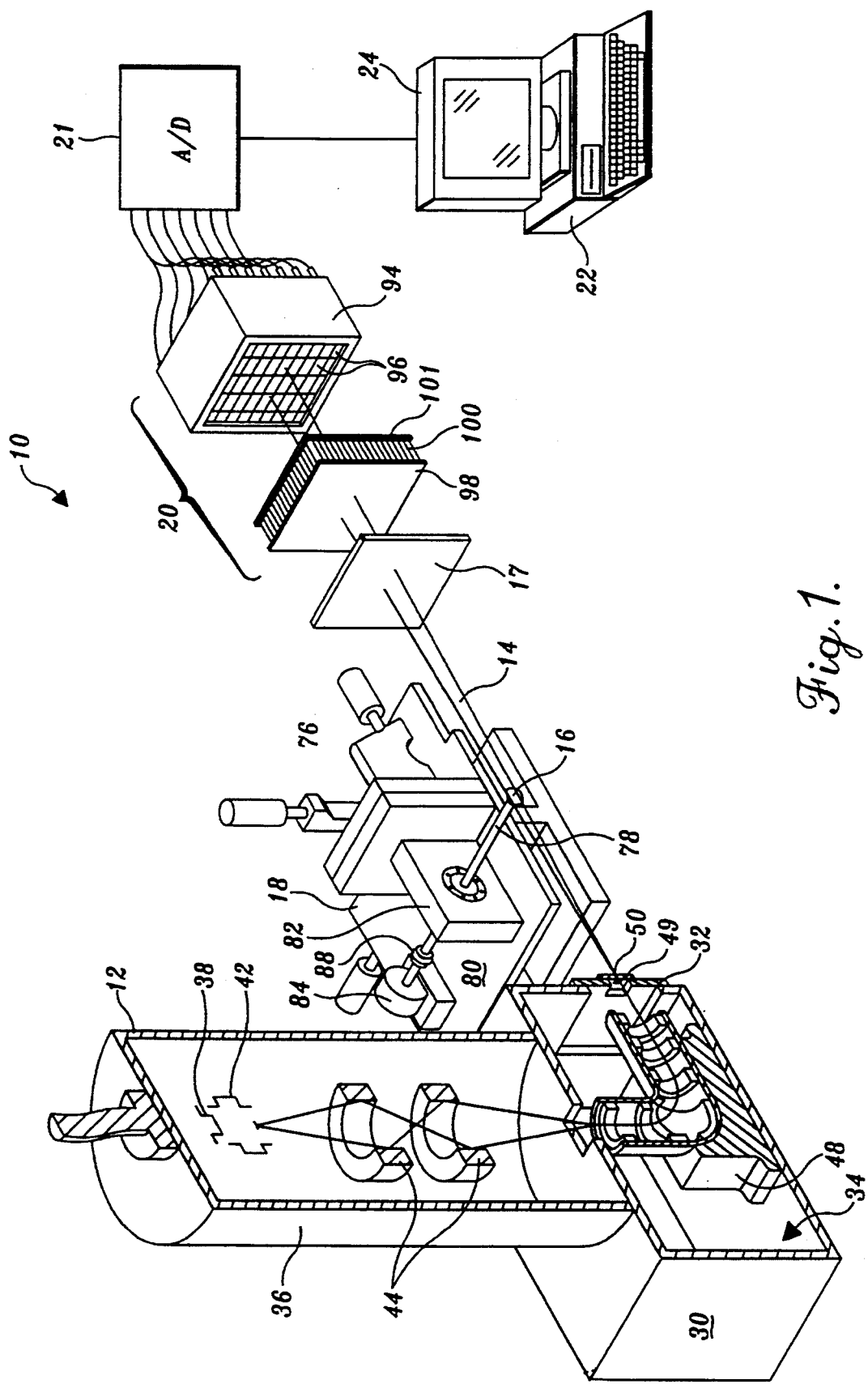
FIG. 1 is a diagrammatic view of the main system components of the microtomograph of this invention.

A microtomographic system 10 in accordance with the present invention is illustrated generally in FIG. 1. The microtomographic system 10 includes an x-ray generator 12 designed to produce an x-ray beam 14 directed at a specimen 16 being imaged. A specimen holder 18 is used to position the specimen 16 laterally, while allowing the specimen to be rotated about an axis that is perpendicular to the x-ray beam 14. An x-ray detector 20, which preferably comprises a charge coupled device, is located beyond the specimen holder 18 and responds to the integrated energy of the x-rays transmitted through the specimen 16. A filter 17, located between the source of the x-rays and the x-ray detector, shifts the effective energy spectra peaks of the x-rays arriving at the detector 20. The analog signals produced by the charged coupled device comprising x-ray detector 20 are converted into digital signals by an analog-to-digital converter 21, and these digital signals are supplied to a processor 22.

The processor 22 generates three-dimensional images of the specimen 16 according to a series of steps described hereinafter. These images, in addition to providing a visual representation of the specimen 16, also provide quantitative information about the phase fractions of the material forming the specimen. The images can be viewed on a display 24 or reproduced in hard copy form on an appropriate printing device.

The x-ray generator 12 of this invention may be constructed from discretely assembed components or alternatively, may comprise a reconstructed scanning electron microscope (SEM), such as an SEM Model No. 840, sold by Japan Electron Optics Company Ltd. of Tokyo, Japan. The x-ray generator 12 includes a generally rectangular base 30 in which a retractable specimen drawer 32 is disposed. The interior of the specimen drawer 32 serves as a specimen chamber 34 in which the specimen to be scanned by the electron beam is positioned. A column 36 that is closed at the top is seated on the base 30. An electron-emitting filament 38 is mounted near the top of the column 36 and is formed of a material that readily gives off electrons when it is subject to a high electrical potential. To reduce the potential required, the electron-emitting filament may be heated with an electrical current. Suitable filaments 38 include thermally assisted tungsten, lanthanum hexaboride ($LAB_6$), or field emission filaments such as Scottky field emitters. High voltage anodes 42 are mounted around the filament 38 to produce the necessary electrical field potential. A set of selectively charged coils 44, that function as electron beam focusing lenses, are mounted in the chamber 36 below the anodes 42. The electron beam produced by the filament 38 and focused by the coils 44 is directed into the base 30, through the coil 44 that is closest to the base.

The electron beam is directed outward toward the face of the base 30 by a deflector assembly 48 mounted in the base 30. Deflector assembly 48 deflects the electron beam to strike a foil target 50 that is secured to the face of the base 30. More particularly the foil target 50 is mounted to a window 49 formed of beryllium or other suitable low atomic number material that is sealed and secured to a small opening formed in the face of the base. The foil target 50 is a high atomic number metal such as gold, platinum, cobalt, copper, molybdenum, tungsten, silver, or aluminum. The target 50 and window 49 can also be mounted to an opening formed in the specimen drawer 32. The specimen drawer 32 is constructed so that it can be vacuum sealed to the base 30. In this embodiment of the invention, the deflector assembly 48 is seated in the bottom of the specimen drawer 32.

The electron beam generating components of the x-ray generator are configured to generate an electron beam with a potential between 0.5 and 50 keV. For a microtomographic system 10 capable of quantitizing hard tissue/soft tissue phase fractions of biological specimens, it has been found necessary to provide an x-ray generator 12 capable of generating a first, low energy, electron beam having a potential between 20 and 30 keV, i.e, more specifically 25 keV, and a second, high energy, electron beam having a potential between 35 and 45 keV, i.e., more specifically 40 keV.

The coils 44 that function as the electron beam focusing lenses serve two functions. First, the coils 44 focus the beam so that when it strikes the target 50, it has a diameter of approximately 0.1 to 10 microns. Secondly, the coils 44, in combination with the deflector 48, direct the electron beam so that it strikes the target 50 at different points on its surface. In particular, the coils 44 can be adjusted so that the electron beam will selectively strike anywhere within a 1 cm$^2$ area at the center of the target 50.

Figure 2:
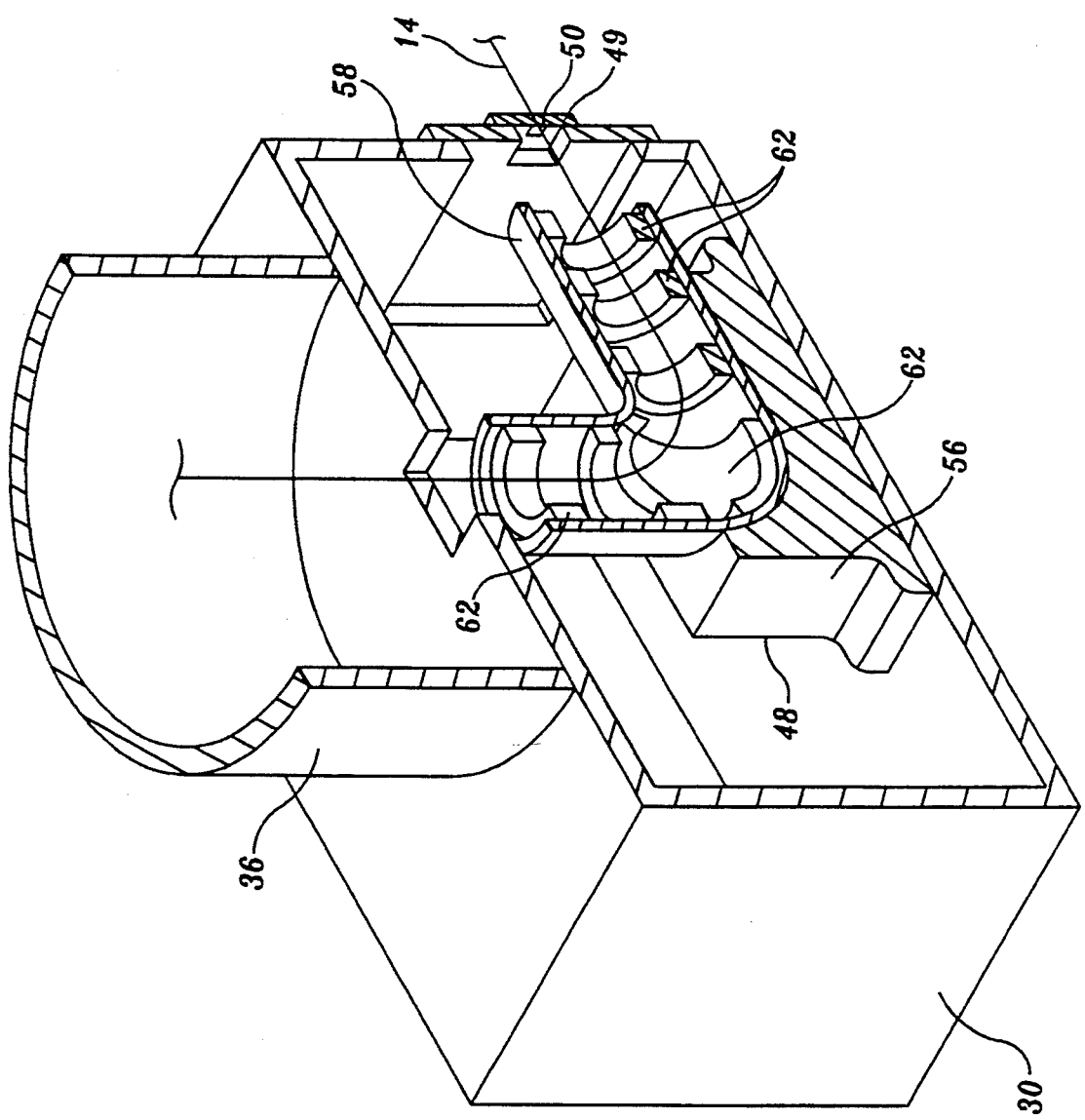
FIG. 2 is a cross-sectional view of an electron beam deflector incorporated into the x-ray generator of this invention.

The electron beam deflector assembly 48, as shown in FIG. 2, includes a base 56 to which an elbow shaped deflection tube 58 is attached. The deflection tube 58 is formed of non-magnetic stainless steel and is shaped like an elbow so as to define a curved bore 60 that extends between the ends of the tube. A set of coils 62 are mounted in the tube 58 such that they extend around its bore 60. A first coil 62 is mounted around the mouth of the tube 58; this coil is selectively energized to finally focus the electron beam as it enters the bore 60. A set of irregularly shaped coils 62 are mounted around the bend in the tube 58, and in combination with the other coils 62 of the deflector, serve to diffuse and bend the electron beam so that instead of being directed vertically downward, it projects outward at an angle between 30° and 150° from its original vertical trajectory. Another coil 62, disposed around the tail end of the tube 58, refocuses the beam as it leaves the bore 60.

The specimen holder 18 is designed to hold a specimen 16 having a maximum dimension of from 0.1 to 50 mm, in a stable position. The specimen holder 18 is further designed to rotate the specimen 16 around an axis that may be perpendicular to that of the x-ray beam 14, and to when necessary shift (i.e., translate) the specimen in x, y, and/or z orthogonal directions. As depicted by FIG. 1, a preferred specimen holder comprises a multi-axis stage 76 to which a precisely positionable shaft 78 is mounted. The multi-axis stage 76 comprises, for example, the Model No. 461-XYZ multi-axis stage manufactured by the Newport Company of California, to which a horizontal bed 80 is mounted. The shaft 78 is mounted to the stage bed 80 by an air bearing spindle 82 or other precision bearing that can be precisely rotated in order to ensure that the specimen 16 is in the correct axial position relative to the x-ray beam 14. One suitable air bearing spindle is the Model No. 4B spindle sold by the Professional Instruments Company of Minneapolis, Minn. The angular position of the shaft 78 is monitored by an optical encoder 84. Integral with the encoder is a stepper motor, not separately illustrated, that controls the position of the shaft 78. The output signals produced by the encoder 84 are supplied to the processor 22. The processor is also connected to the stepper motor for supplying the control signals thereto. The processor 22 monitors the angular position of the shaft and in response to that information, selectively actuates the stepper motor in order to position the shaft. The specimen 16 is secured to the end of the shaft by adhesive, a vacuum drawn through the spindle, or other appropriate means that does not affect the transmission of the x-rays through the specimen. In the illustrated preferred embodiment of the invention, the shaft 78 is separated into two sections between the spindle 82 and the encoder 84, and these two sections are connected by a low torque bellows coupling 88.

The x-ray detector 20 integrates the energy of the x-rays that are transmitted through the specimen 16 so that a measure of the percentage of the x-ray beam absorbed by the specimen can be determined. The detector 20 of FIG. 1 comprises a charge-coupled device 94 that includes an array of light-sensitive detector elements, or pixels 96, each of which produces an analog voltage signal that is a function of the quantity of light striking the light-sensitive detector element. A scintillator layer 98, which converts x-rays into light that can be monitored by the detector elements, is disposed toward the specimen side of the charge coupled device 94. The scintillator layer 98 is formed from a phosphor or crystalline substance that emits light, in wave bands to which the charge-coupled device pixels 96 are most sensitive and which will not degrade the detector's performance over time. Many charge coupled-devices are known to be suitable to monitor the emission red light. Accordingly, the x-ray detector 20 has a scintillator layer 98 formed of $Y_2O_3$:Eu, $Y_2O_2S$:Eu, and $(ZnMg)_3(PO_4)_2$:Mn, since these phosphors have been found to emit red light of the requisite wavelengths. Typically the phosphor forming the scintillator layer 98 is approximately 20 to 200 $\mu$m thick.

In the illustrated preferred embodiment of the invention, a set of small, pixel sized fiber optic cables 100 separate the scintillator layer from the exposed faces of the pixels 96 and serve as conduits for the light to the pixels. The light transmitted through the fiber optic cables 100 is focused on the pixels 96 by a lens 101. In another embodiment of the invention (not shown), the fiber optic cables are omitted and multiple lenses are employed to project the light directly onto the pixels 96.

The light generated by the scintillator layer 98 in response to the energy of x-ray beam 14 will vary in intensity between $10^{-9}$ to 10 lux. The charge-coupled device 94 that monitors this light should have a relatively high signal-to-noise ratio, i.e., between 20 and 1000, or higher, for measuring the low levels of light that might be emitted by the scintillator layer 98.

The x-ray detector 20 is positioned relative to the x-ray source and specimen 16 so that the spatial resolution of the resultant image is not limited by the pixel size of the detecting elements or the scintillator layer 98 thickness. For example, a charge coupled device-type detector typically has light sensing pixels 96 that are approximately 25 $\mu$m in diameter. Accordingly, if this type of detector assembly is positioned 10 to 20 cm from the source of the x-ray beam 14, images having a spatial resolution on the order of 1 $\mu$m can be created.

The filter 17 is provided to more effectively resolve the spectral energy of the high and low energy x-rays using the x-ray detector 20. In FIG. 1, the filter is mounted immediately in front of the scintillator layer 98. The filter is preferably a thin plate of metal, such as aluminum, that changes the effective energy level of the x-rays by attenuating a substantial portion of the x-rays at a selected energy level. In the embodiment of the invention used to image biological tissue samples, an aluminum plate approximately 25 microns thick is used to filter the low energy spectra x-ray beam, minimizing the low energy x-ray noise reaching the x-ray detector 20. An aluminum plate approximately 300 microns thick is used to filter the high energy spectra x-ray beam. This filtering of the high energy beam is performed to reduce the overlap between the dtected energy spectra of the high and the low energy spectra x-rays. The resulting increased spacing of the energy levels between the different energy x-rays makes it easier to determine the composition, or phase, of the material forming the specimen 16 in the processing steps to be discussed hereinafter. While the filter 17 is shown as being associated with the x-ray detector 20, it could alternatively be disposed between the source of the x-rays and the specimen 16. For example, the filter 17 could be attached to the x-ray generator 12 in front of the window 49.

The analog-to-digital signal converter 21 converts the analog signals representative of luminescence produced by the x-ray detector 20 into equivalent 12 to 16-bit digital signals that can be processed by the processor 22. These digitized luminescence signals are forwarded to the processor 22, which then produces the final images of the specimen 16.

The steps by which the microtomographic system 10 of this invention generates an image of a specimen are now described. Throughout this description, it should be understood the term "projection" means a particular individual two-dimensional recording of the x-ray transmission through the specimen 14; "view" describes the orientation, or position of the specimen relative to the x-ray beam when the projection is made; and "image" means the final representation of the specimen based on the processing of the individual projections. Initially, a set of "flood field" projections are made. These are projections that are made when the x-ray beam 14 is applied directly to the x-ray detector 20 without placing a specimen in the path of the beam. These projections are made in order to determine the intensity of the x-rays incident on the specimen at each pixel 96 in the detector 20, so that, as described hereinafter, the non-uniform intensity may be corrected and the content of the specimen can be determined. An individual flood field projection is made for each unique energy spectrum x-ray beam 14 that is subsequently used to form the individual projections of the specimen.

The flood field projections, as well as the subsequent projections, are made by developing a potential between the filament 38 and the anodes 42 that causes an electron beam to develop. The electron beam is focused to the selected spot size by the development of the appropriate potentials around the lens focusing coils 44. The electron beam then enters into the deflector assembly 48 and is bent horizontally outward toward the target 50. The energy of the electron beam absorbed by the target 50 causes the metal forming the target to emit an x-ray beam 14. Since the electron beam has a circular, or spot profile, the x-ray beam at its source point, the surface of the target 50, has a similar profile. As the x-rays forming the beam 14 move away from the target 50 they diverge outwardly from the source axis in two dimensions so that the x-ray beam has a conical shape.

Figure 3:
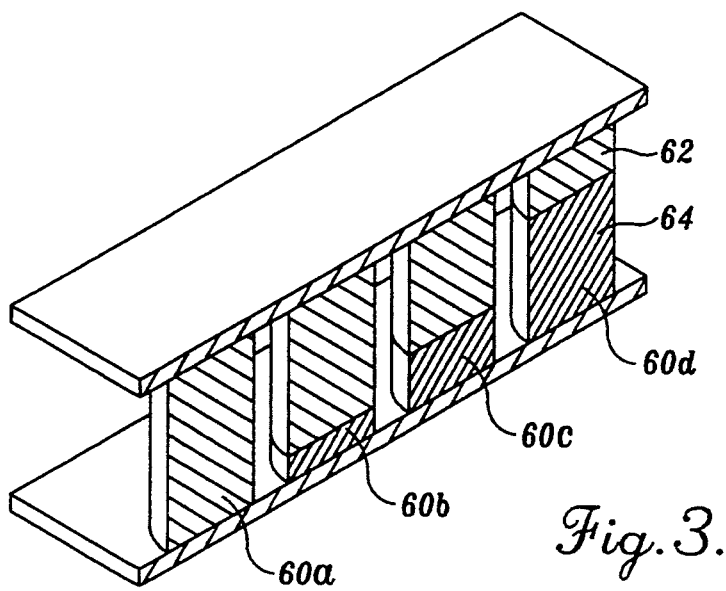
FIG. 3 is a side view of a set of phantom specimens, which are used by the system of this invention to provide data from which information regarding the phase fractions of the material forming the specimen being imaged can be obtained.

After the flood field projections are made, a series of projections of a set of phantom specimens 60a, 60b, 60c ..., depicted in FIG. 3, are made. Each phantom specimen 60a, 60b, 60c, ... contains a known phase fraction of one of the components of the specimen 14 being imaged. For example, if the specimen being imaged is a biological tissue sample, and it is being imaged to determine its hard tissue/soft tissue phase fractions, projections of a set of phantom specimens containing 0%, 1%, 2%, 3%, 4%, 5%, 10%, 20%, 30%, and 70% hard tissue can be made.

With regard to the imaging of biological specimens, it has been found that an acrylic plastic 62, such as that sold under the trademark "LUCITE," have x-ray absorption characteristics similar to that of nerves, muscle and other soft tissue, and that hydroxyapatite, $3Ca_3(PO_4)_2.Ca(OH)_2$, 64 has absorption characteristics similar to that of bone or hard tissue. Accordingly, a set of phantom samples 60a, 60b, 60c, ... can be constructed out of small discs of acrylic plastic that are disposed in wells of material that is substantially transparent to x-rays; the wells are then filled to various depths with hydroxyapatite grout.

A portion of the x-rays from each beam 14 that strikes the phantom specimens 60, as well as the specimen 16 being imaged are attenuated by the specimen either by internal absorption of the beam or by beam scattering. The remaining fraction of the x-rays are transmitted through the specimen. The x-ray detector 20 measures, on a pixel by pixel resolution, the percent of x-rays that pass through each point in the specimen 16 (by comparison to the flood field projections made without a specimen). In practice, for specimens comprised of two different types of matter, i.e., those with two phases of interest, two projections, one with x-ray beam 14 that is created in response to the generation of the low voltage electron beam and second one with a beam that is created in response to the generation of a high voltage electron beam are taken of each phantom sample. Since these beams are created by electron beams that have different potentials, the x-ray beams themselves have different energy spectra.

Once the projections of the phantom samples are created, a set of projections of a number of different views of the specimen 16 are made. Two projections of each view of the specimen 16 are made: one view is made from an x-ray beam 14 produced by the low energy spectra x-ray beam; and the second view is made from the high energy spectra x-ray beam. Once the set of projections for a particular view of the specimen 16 have been made, the specimen holder 18 is adjusted to translate and/or rotate the specimen so that a second set of projections can be made of the specimen at a different view. This process of making sets of projections for the specimen at different views is repeated until there are sufficient number of projections of different views to create a three-dimensional image of the specimen. Preferably, a minimum 180 sets of projections should be taken from views 2° apart in order to create a three-dimensional image. More ideally, it is preferred that the number of sets of projections of different views of the specimen 16 be at least equal to the pixel resolution of the x-ray detector 20. For example if the x-ray detector 20 comprises a grid of 256 pixel elements×256 pixel elements, at least 256 sets of projections of different, equal angularity, axially separated views of the specimen 16 should be made. If the x-ray detector 20 includes a grid of 1024 by 1024 pixel elements, at least 1024 sets of projections of different, angularly separated views of the specimen should be made.

Once the requisite projections have been made, the process of analyzing their data to create the resultant images begins. The analog-to-digital converter 21 converts the analog signals produced by the light-sensitive pixels 96 into digital signals and forwards the digital signals to the processor 22 so that a bit map representative of the integral of the incident x-ray energy level that is transmitted through a particular path in the specimen 16 can be generated.

Once the x-ray data are digitized, the data are processed to quantify the phase fractions of the material depicted in each view of the specimen. This determination is based upon the fact that x-ray attenuation is inversely proportional to the cube of the energy of the beam and is directly proportional to the density of the specimen being imaged. Accordingly if a particular specimen consists of two different components, each of which has a different density, and if the specimen is exposed to two x-ray beams having different energy characteristics, the transmitted intensity through the specimen as measured through a given line can be calculated according to the following formulas:

$$\ln(I/Io)_{low} = b_0 + b_1A_1 + b_2A_2 + b_3A_1^2 + b_4A_2^2 + b_5A_1A_2 + b_6A_1^3 + b_2A_2^3 \quad (1)$$

$$\ln(I/Io)_{high} = c_0 + c_1A_1 + c_2A_2 + c_3A_1^2 + c_4A_2^2 + c_5A_1A_2 + c_6A_1^3 + c_2A_2^3 \quad (2)$$

In these formulas: I is the x-ray intensity transmitted by the specimen, Io is the intensity of the flood field, (the incident energy on the detector assuming no absorption of the x-rays); $b_i$ and $c_i$ are unknown coefficients; and $A_1$ and $A_2$ are the thicknesses of the different material comprising the sample.

Since the values of I, Io, $A_1$, and $A_2$ for the two different x-ray energy spectra projections of the phantom samples are known, $b_i$ and $c_i$ can be calculated. For a set of projections of the specimen 16, the values of I and Io are known. Thus, since the coefficients $b_i$ and $c_i$ are calculated from the projections of the phantom specimen, $A_1$ and $A_2$ can then be calculated through any line through the specimen 16 as measured in the line from the x-ray source point to the pixel receiving the incident and transmitted energy.

Figure 4A:
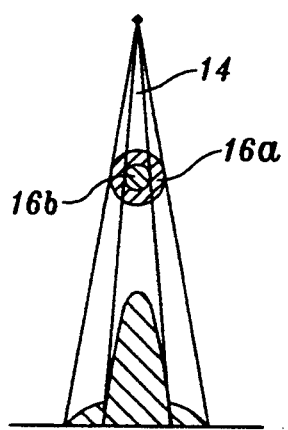
FIGS. 4A–4C diagramatically depicted the incident energy measured using a projection of a two-phase specimen taken according to this invention, and the resultant processed phase data that quantify the composition, or phase structure, of the specimen.
Figure 4B:
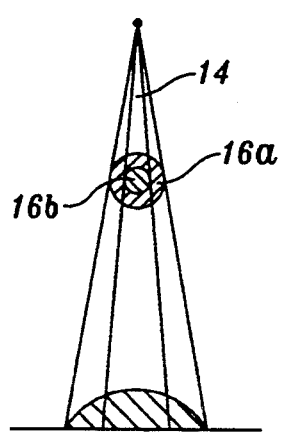
Figure 4C:
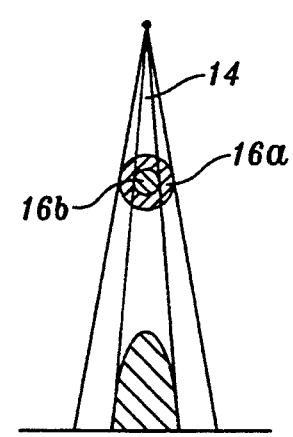

The data upon which this processing is based and the data produced by this processing are illustrated diagramatically in FIGS. 4A–4C. In each of these FIGURES the specimen 16 is depicted as having a bone core 16a that is surrounded by an annulus of soft tissue 16b. FIG. 4A represents a slice of the raw data collected in a single projection of the specimen 16 with x-rays of a given energy spectrum. As can be seen in this FIGURE, the fraction of incident energy transmitted through the portion of the specimen that comprise both bone and soft tissue is substantially different than the fraction of the incident energy transmitted through the soft tissue alone. The processing of the data collected in the projections made with x-rays at two different energy levels yields the processed projection data diagramatically depicted by FIGS. 4B and 4C. As seen in these FIGURES the processing indicates the phase fraction of both the soft tissue and bone components of the specimen at each point along the slice of the specimen.

After the processed projections, which are bit maps of the phase fractions of the material forming the specimens for the individual points of the views are generated, the data are further processed using a set of conebeam projection algorithms to generate a three-dimensional image of the specimen. One such formula that can be used to generate the image is the following convolution backprojection formula:

$$f(r) = \frac{1}{4\pi^2} \int d\Phi \frac{d^2}{(d + r \cdot x')^2} P_\Phi[Y(r), Z(r)], \quad (3)$$

where $f(r)$ represents the x-ray attenuation function of the specimen at the point at the end of vector r, which originates from the center of the specimen coordinate system, $\Phi$ represents the angle of rotation between the x-axis of a coordinate system that rotates with the specimen and the normal between the source and the x-ray detector 20, which defines the x-axis of the stationary coordinate system; $P_\Phi[(Yr), Z(r)]$ is the filtered, projection data, weighted once before filtering to compensate for the fact that while beam has constant intensity or sampling density over a spherically shaped surface, the intensity of the beam is measured over a flat surface; and wherein $[d/(d+r\cdot x')^2]$ is a second weighting factor that compensates for the cone beam geometry employed for the backprojection to obtain $f(r)$.

The weighted coordinates of the projection data, Y(r) and Z(r), are calculated according to the following formula:

$$Y(r) = r \cdot y'd/(d + r \cdot x'), \quad (4)$$

$$Z(r) = r \cdot z'd/(d + r \cdot x'), \quad (5)$$

where d is the distance between the between the source and the axis of rotation of the specimen; y' is the unit vector defining the horizontal direction along the detector rotated through angle $\Phi$ with respect to the source-detector axis; and z' is the unit vector orthogonal to both y' and x'.

The projection data, P[Y, Z], which is the calculated $A_1$ or $A_2$ value representative of the fraction of the hard tissue or soft tissue measured at a specific point, is filtered to allow the spectrum attenuation function to be recovered by conebeam backprojection of the filtered data. The filtered projections are calculated according to the following formula:

$$P_\Phi(Y,Z) = \int_{-\infty}^{\infty} dY' \int_{-\infty}^{\infty} dZ' g_y(Y - Y') g_z(Z - Z') \times \quad (6)$$

$$P_\Phi(Y',Z')d/(d^2 + Y^2 + Z^2)^{\frac{1}{2}}$$

In this formula: Y is the direction on the detector perpendicular to the specimen axis of rotation; Z is the direction on the detector parallel to the axis of rotation; Y' and Z' are the variables of integration; and $g_y$ and $g_z$ are the convolution kernels in the Y and Z directions, respectively. These kernels are calculated according to the formulas:

$$g_y(Y) = Re \int_0^{\omega_y 0} \omega d\omega \exp(i\omega Y), \quad (7)$$

-continued
$$g_z(Z) = \sin \omega_{z0} Z / \pi Z. \qquad (8)$$

In these formulas, $\omega$ represents the spatial frequency in the specimen, which in practice is limited to $\omega_{y0}$ and $\omega_{x0}$ by the combination of detector pixel size, projection magnification of the specimen onto the detector plane and application of the Nyquist criterion. Moreover, in practice the convolution in the Z direction need not be performed in order to obtain the desired results. A more complete understanding of these, formulas can be found in Feldkamp et al., "Practical Cone-Beam Algorithm," Journal of the Optical Society of America A—Optics and Image Science, Vol. 1. No. 6, June 1984 p. 612, which is incorporated herein by reference.

Since the data from the x-ray detector 20 are available from discrete locations, the individual pixel points, and the specimen 16 is rotated with a discrete, known angularity, discrete versions of the above-described equations are employed by the processor 22 to generate the $f(r)$ data upon which the final images are created. During this processing, the processor substitutes the calculated values of $A_1(Y,Z)$ and $A_2(Y,Z)$, the composition or phase fraction values of the material present at point (Y,Z) for $P_\Phi(Y',Z')$. Once the $P_\Phi$ values are calculated, the processor 22 can then calculate the image intensity for any point in the specimen so as to generate a three-dimensional image of the specimen based on data that quantitatively indicates the composition or phase fraction of the specimen 16 being imaged.

The microtomographic system 10 of this invention thus serves as a convenient device for providing high-resolution, three-dimensional images of a specimen. Furthermore, the images produced by this system provide quantitative information regarding the phase fraction of the material that comprises the specimen. Furthermore, this system produces three-dimensional images with only a single x-ray generator 12 and corresponding x-ray detector 18, thereby minimizing both the cost of the system and its physical size. Still another advantage of the microtomographic system 10 is that the x-ray beam 14 is created in the ambient environment. Thus, this system 10 is well suited to provided images of biological tissue samples and other specimens that would rapidly change character if the imaging took place in a vacuum environment. Still another advantage of the microtomographic system 10 is that the electron beam used to produce the x-ray beam is deflected horizontally so that it produces an x-ray bean that projects away from the x-ray generator 12, making it possible to selectively locate the specimen and x-ray detector apart from the x-ray generator as required to ensure that projection and images with the desired spatial resolution can be produced.

Figure 5:
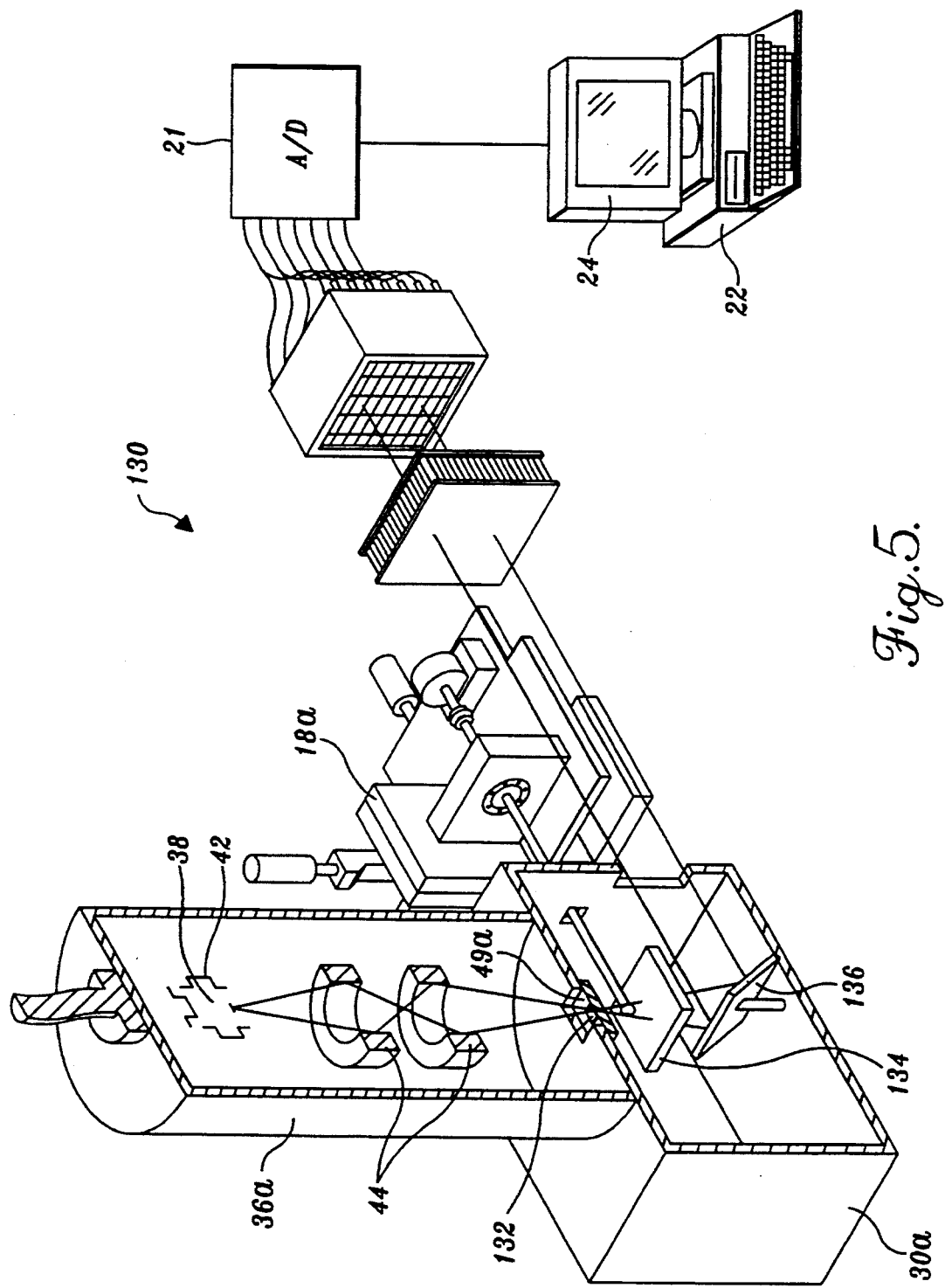
FIG. 5 is a diagrammatic view of an alternative embodiment of the microtomograph of this invention.

FIG. 5 illustrates an alternative embodiment, microtomographic system 130. Microtomographic system 130 has the same basic electron beam generating components as the first described embodiment of this invention and is constructed so as to have a foil target 132 seated in the bottom of the column 36a. Specimen holder 18a is configured to hold the specimen 16 at a selected distance below the foil target 132. A scintillator 134 is positioned in the base 30a of the system below the specimen 16. A mirror 136 is located in the bottom of the base below the scintillator 134. The mirror 136 directs the light emitted by the scintillator 134 outward where it is measured by the x-ray detector 20.

An advantage of microtomographic system 130 is that it eliminates the need to mount the x-ray detector inside the x-ray generator. It thus provides an economical alternative embodiment that still allows the x-ray detector to be selectively positioned relative to the x-ray source so as to obtain some control over the spatial resolution of the resultant projections and images.

It should be recognized that the foregoing descriptions are for the purposes of illustration only and the invention can be practiced using equipment and methods different than those described above. For example, there is of course no need to use a converted SEM as the electron gun to cause the emission of the requisite x-rays, or even to use an electron gun to generate the x-ray beam 14. As a further contemplated modification, plasma source x-ray detectors may be employed. Furthermore, detectors other than the described charge-coupled device may be used to measure the x-rays transmitted through the specimen being imaged. For example, in some instances it may be desirable to employ stimulable phosphor plates as the detectors. The material in these plates becomes excited in proportion to the intensity of x-rays to which they are exposed. Once a plate is exposed, a laser beam is used to further excite the phosphor material to the point where it gives off light in proportion to the intensity of the x-ray beam to which it was initially exposed. The intensity of this visible light is measured in order to provide an indication of the transmissivity of the specimen to the x-rays. Still in other embodiments of the invention, x-ray sensitive photograph film may be employed as the detecting element.

It should also be recognized that the processes by which the image of the specimen are created may be different from what has been disclosed. For example, it may be possible to obtain quantitative information about the composition of a specimen formed of three or more different types of matter. This information can be obtained by making three or more projections of each view of the specimen, wherein each projection is made with an x-ray beam having a distinct energy spectra, and the total number of different x-ray spectra employed is equal to the number of different types (density) of material comprising the specimen being imaged. Once projections of phantom specimens containing known ratios of the several phases of interest in the specimen and the multiple projections of the specimen are made, the basic transmitted energy and flood field energy equations can then be expanded to provide an accurate indication of the composition of the specimen.

It should also be recognized that the x-ray source from which the x-ray beam 14 emanates need not always be at a constant location. It may be desirable in some instances to shift the electron beam so that the resultant x-ray beam is centered on different points relative to the center of the specimen 16. The movement of the x-ray beam 14 in combination with the rotation of the specimen can be used to create a pattern of views for which the source describes no-circular trajectories relative to the specimen. For example, it may desirable to shift the x-ray source and/or shift and rotate the specimen to create a set of projections that follows a curve, similar to that of the stitching around a baseball. An advantage of creating projections using such alternative source trajectories is that they provide more robust data sets for input into conebeam reconstruction algorithms. Such data are more immune to artifacts caused by low signal-to-noise ratios in the detector assembly or low x-ray energy levels at the detector. The accuracy with which the composition of the specimen may be calculated and with which structural detail in the specimen may be rendered is higher for non-circular loci of x-ray source points than it is for greater circles, because the systems of equations used to determine the phase-fraction processed projections and to obtain the three-dimensional object function from the processed projections are more stable when more projection data sets obtained from non-circular source trajectories are used.

Therefore, it is the object of the appended claims to cover all such modifications and variations as come within the true spirit and scope of the invention.

The embodiments of the invention in which an exclusive property or privilege is claimed are defined as follows:

1. A data acquisition method for microtomographic analysis of a specimen, the specimen comprising varying phase fractions of first and second types of material, the method including the steps of:
   a. making a plurality of sets of projections of the specimen, each projection of the specimen being a measure of the incident energy (I) of a conebeam x-ray transmitted from an x-ray source through the specimen to a detector, said detector having a plurality of x-ray sensitive pixels and each set of projections including a first projection of the specimen of a selected view, wherein said x-rays used to make said first projection have a first energy spectra, and a second projection of the specimen of a selected view, wherein said x-rays used to make said second projection have a second energy spectra different from said first energy spectra, and wherein each set of projections are made of different selected views of the specimen;
   b. quantifying the phase fraction of the material forming the specimen for each said selected view of the specimen by evaluating the differences in said incident x-ray energy transmitted through the specimen between said first and second projections of said specimen at each of the detector pixels for each set of projections, wherein said quantifying process for each set of projections of the specimen produces a first processed projection representative of the phase fraction of a first type of material forming the specimen and a second processed projection representative of the second type of material forming the specimen; and
   c. calculating the phase fraction of the material forming the specimen at a selected point in the specimen by performing backplane analyses of said processed projections, wherein a first backplane analysis is performed of said first processed projections to obtain an indication of the phase fraction of the first type of material forming the specimen at said selected point and a second backplane analysis is performed of said second processed projections to obtain an indication of the phase fraction of said second type of material forming the specimen at said selected point.

2. The data acquisition method of claim 1, further including the steps of positioning said specimen and said x-ray detector relative to said x-ray source so that said projections depict the features of the specimen to micron-order spatial resolution.

3. The data acquisition method of claim 1, wherein said step of quantitizing the phase fractions of the material forming the specimen includes the steps of:
   a. making a plurality of flood field projections, wherein each said flood field projection is a measurement of the incident x-ray energy (Io) transmitted from said x-ray source to said x-ray detector without having the specimen located therebetween, and wherein a first flood field projection is made for said x-ray beam having said first energy spectra and a second flood field projection is made for said x-ray beam having said second energy spectra;
   b. making sets of projections of at least two phantom specimens, each said phantom specimen having x-ray transmission characteristics identical to that of a sample of the specimen with a known phase fraction of the material forming the specimen, wherein a first projection of each set of projections is made with an x-ray beam having said first energy spectra and a second projection of each set of projections is made with an x-ray beam having said second energy spectra; and
   c. calculating said phase fractions of the material forming the specimen based on I/Io ratios for said first and second projections at said pixel, and on a plurality of variables for said pixel determined by a set of I/Io ratios of said sets of projections of said phantom specimens.

4. The method of data acquisition of claim 1, wherein said sets of projections of said different views of the specimen are obtained by rotating the angular alignment of said specimen relative to said x-ray source and said x-ray detector.

5. The method of data acquisition of claim 1, wherein said sets of projections of said different views of the specimen are obtained by shifting a translational alignment of the specimen relative to said x-ray source and said x-ray detector.

6. The method of data acquisition of claim 5, wherein said sets of projections of said different views of the specimen are further obtained by rotating an angular alignment of said specimen relative to said x-ray source and said x-ray detector.

7. The method of data acquisition of claim 1, further including the step of filtering said x-rays used to make one of said first and second projections so as to better resolve said energy spectra of said x-rays.

8. An x-ray microtomograph for making x-ray projections of a specimen, comprising:
   a base having an interior space, an open face and a top located opening;
   an electron gun assembly disposed on top of said base, said electron gun assembly configured to produce a downward directed electron beam through said base top located opening and into said interior space of said base;
   an electron beam deflector located in said interior space of said base, said electron beam deflector positioned to deflect said downward directed electron beam away from the vertical and toward said open face of said base;
   a face plate secured over said open face of said base so as to have a vacuum-tight seal, said face plate including an opening, wherein said face plate opening is positioned so that said electron beam is directed toward said opening; and a target located in said face plate opening, said target being formed of a material that emits x-rays upon being struck by said electron beam so as to produce an x-ray beam directed away from said base.

9. The microtomograph of claim 8, further including: a specimen holder positioned outside of and spaced apart from said base, for holding the specimen in the path of said x-rays; and an x-ray detector spaced apart from said specimen holder.

10. The microtomograph of claim 9, wherein, said electron gun assembly and said electron beam deflector are configured to produce an electron beam that forms a spot on said target having a diameter of approximately one micron, and said specimen holder and said x-ray detector are positioned relative to said base so that x-ray projections measured by said x-ray detector have a spatial resolution of micron-order.

11. An x-ray microtomograph for making x-ray projections of a specimen, comprising:
a base having an interior space and an open face, said base being further formed with a top located opening;
an electron gun assembly disposed on top of said base, said electron gun assembly configured to produce an electron beam directed vertically downward toward said top located opening of said base;
a target mounted in said top located opening of said base, said target being formed of a material that emits x-rays in response to being struck by said electron beam, said x-rays having an incident energy;
a specimen holder positioned adjacent said base for positioning the specimen in the path of said x-rays;
a scintillator layer located in said base and positioned below the specimen for emitting visible light in proportion to the energy of x-rays transmitted through the specimen;
a reflector disposed in said base and positioned to reflect light emitted by said scintillator layer out through said open face of said base; and
a detector adjacent said base for measuring said light emitting by said scintillator layer as a measure of incident x-ray energy transmitted through the specimen.

12. The microtomograph of claim 11, wherein said electron gun is configured to produce an electron beam that forms a spot on said target having a diameter of approximately one micron, and said specimen holder is positioned relative to said target and said x-ray detector is positioned relative to said reflector sufficient distances apart so that said x-rays measured by said x-ray detector has a spatial resolution of micron-order.

* * * * *

UNITED STATES PATENT AND TRADEMARK OFFICE
CERTIFICATE OF CORRECTION

PATENT NO. : 5,402,460
DATED : March 28, 1995
INVENTOR(S) : R.H. Johnson et al.

It is certified that error appears in the above-indentified patent and that said Letters Patent is hereby corrected as shown below:

| COLUMN | LINE | |
|---|---|---|
| Title Page, | [56] Refs. Cited Other Pubs | "Microscopy", should read --Microscope",-- |
| 10 | 11 | "$\int d\phi$" should read --$\oint d\phi$-- |
| 10 | 34 | "y' " should read --$\hat{y}$'-- |
| 10 | 34 | "x' " should read --$\hat{x}$'-- |
| 10 | 36 | "z' " should read --$\hat{z}$'-- |
| 10 | 33 | "x' " should read --$\hat{x}$'-- |

UNITED STATES PATENT AND TRADEMARK OFFICE
CERTIFICATE OF CORRECTION

PATENT NO. : 5,402,460
DATED : March 28, 1995
INVENTOR(S) : R.H. Johnson et al.

It is certified that error appears in the above-indentified patent and that said Letters Patent is hereby corrected as shown below:

| COLUMN | LINE | |
|--------|------|---|
| 10 | 37 | "y' " should read --$\hat{y}'$-- |
| 10 | 40 | "z' " should read --$\hat{z}'$-- |
| 11 | 11 | "these," should read --these-- |

Signed and Sealed this

Twenty-fifth Day of July, 1995

BRUCE LEHMAN

Attest:

Attesting Officer

Commissioner of Patents and Trademarks